United States Patent
Mazlish

(10) Patent No.: US 11,376,362 B2
(45) Date of Patent: *Jul. 5, 2022

(54) SYSTEMS FOR DETERMINING INSULIN ON BOARD AND RECOMMENDING INSULIN THERAPY AND RELATED METHODS

(71) Applicant: Bigfoot Biomedical, Inc., Milpitas, CA (US)

(72) Inventor: Bryan Mazlish, Palo Alto, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 742 days.

This patent is subject to a terminal disclaimer.

(21) Appl. No.: 16/213,799

(22) Filed: Dec. 7, 2018

(65) Prior Publication Data

US 2019/0105444 A1 Apr. 11, 2019

Related U.S. Application Data

(63) Continuation of application No. 14/733,567, filed on Jun. 8, 2015, now Pat. No. 10,188,793.

(60) Provisional application No. 62/010,385, filed on Jun. 10, 2014.

(51) Int. Cl.

| | |
|---|---|
| *A61M 5/172* | (2006.01) |
| *G16H 40/63* | (2018.01) |
| *G16H 40/67* | (2018.01) |
| *G16H 50/20* | (2018.01) |
| *G16H 20/17* | (2018.01) |
| *G16Z 99/00* | (2019.01) |
| *A61M 5/142* | (2006.01) |
| *A61B 5/145* | (2006.01) |
| *A61B 5/00* | (2006.01) |

(52) U.S. Cl.
CPC ...... *A61M 5/1723* (2013.01); *A61M 5/14244* (2013.01); *G16H 20/17* (2018.01); *G16H 40/63* (2018.01); *G16H 40/67* (2018.01); *G16H 50/20* (2018.01); *G16Z 99/00* (2019.02); *A61B 5/14532* (2013.01); *A61B 5/4839* (2013.01); *A61M 2005/14208* (2013.01); *A61M 2005/1726* (2013.01); *A61M 2205/18* (2013.01); *A61M 2205/3553* (2013.01); *A61M 2205/3561* (2013.01); *A61M 2205/3584* (2013.01); *A61M 2205/3592* (2013.01); *A61M 2209/01* (2013.01); *A61M 2230/201* (2013.01)

(58) Field of Classification Search
None
See application file for complete search history.

(56) References Cited

U.S. PATENT DOCUMENTS

| | | |
|---|---|---|
| 4,464,170 A | 8/1984 | Clemens et al. |
| 5,822,715 A | 10/1998 | Worthington et al. |
| 5,971,922 A | 10/1999 | Arita et al. |
| 6,081,786 A | 6/2000 | Barry et al. |
| 6,379,301 B1 | 4/2002 | Worthington et al. |
| 6,544,212 B2 | 4/2003 | Galley et al. |
| 6,595,919 B2 | 7/2003 | Berner et al. |
| 6,691,043 B2 | 2/2004 | Ribeiro, Jr. |
| 6,835,175 B1 | 12/2004 | Porumbescu |
| 6,925,393 B1 | 8/2005 | Kalatz et al. |
| 7,025,743 B2 | 4/2006 | Mann et al. |
| 7,137,951 B2 | 11/2006 | Pilarski |
| 7,266,400 B2 | 9/2007 | Fine et al. |
| 7,570,980 B2 | 8/2009 | Ginsberg |
| 7,651,845 B2 | 1/2010 | Doyle et al. |
| 7,766,829 B2 | 8/2010 | Sloan et al. |
| 7,806,854 B2 | 10/2010 | Damiano et al. |
| 7,850,641 B2 | 12/2010 | Lebel et al. |
| 7,920,998 B2 | 4/2011 | Brown |
| 7,949,507 B2 | 5/2011 | Brown |
| 7,979,259 B2 | 7/2011 | Brown |
| RE43,316 E | 4/2012 | Brown et al. |
| 8,147,446 B2 | 4/2012 | Yodfat et al. |
| 8,204,729 B2 | 6/2012 | Sher |
| 8,206,296 B2 | 6/2012 | Jennewine |

(Continued)

FOREIGN PATENT DOCUMENTS

| | | |
|---|---|---|
| JP | 2008-545454 A | 12/2008 |
| JP | 2010-531678 A | 9/2010 |

(Continued)

OTHER PUBLICATIONS

Swan et al.; Effect of age of infusion site and type of rapid-acting analog on pharmacodynamic parameters of insulin boluses in youth with type 1 diabetes receiving insulin pump therapy; Diabetes Care; 32(2); pp. 240-244; Feb. 2009.

(Continued)

*Primary Examiner* — G Steven Vanni
(74) *Attorney, Agent, or Firm* — TraskBritt

(57) ABSTRACT

A system is provided with an insulin delivery device configured to deliver insulin to a user of the system and a computer-based control unit associated with the insulin delivery device. The computer-based control unit includes a user interface and a computer-based processor. The computer-based processor is configured to calculate a relative insulin on board value for a specific time by calculating a first value that represents a reference insulin on board value at the specific time, calculating a second value that represents an automated insulin on board value at the specific time, and subtracting one of the first and second values from the other. The automated insulin on board value represents at least one insulin delivery automatically specified by the computer-based control unit. Methods of use are also disclosed.

18 Claims, 9 Drawing Sheets

(56) References Cited

U.S. PATENT DOCUMENTS

| | | |
|---|---|---|
| 8,257,300 B2 | 9/2012 | Budiman et al. |
| 8,265,726 B2 | 9/2012 | Say et al. |
| 8,273,022 B2 | 9/2012 | Say et al. |
| 8,298,184 B2 | 10/2012 | Diperna et al. |
| 9,833,191 B2 | 12/2017 | Mazlish |
| 10,188,793 B2 | 1/2019 | Mazlish |
| 2003/0163223 A1 | 8/2003 | Blomquist |
| 2004/0220517 A1 | 11/2004 | Starkweather et al. |
| 2005/0038680 A1 | 2/2005 | McMahon |
| 2005/0043598 A1 | 2/2005 | Goode et al. |
| 2005/0272640 A1 | 12/2005 | Doyle et al. |
| 2006/0253067 A1 | 11/2006 | Staib et al. |
| 2007/0060869 A1 | 3/2007 | Tolle et al. |
| 2007/0100222 A1 | 5/2007 | Mastrototaro et al. |
| 2007/0168145 A1 | 7/2007 | Beyer et al. |
| 2008/0201325 A1 | 8/2008 | Doniger et al. |
| 2008/0208113 A1 | 8/2008 | Damiano et al. |
| 2008/0228056 A1 | 9/2008 | Blomquist et al. |
| 2008/0234663 A1 | 9/2008 | Yodfat et al. |
| 2008/0250341 A1 | 10/2008 | Dlugos et al. |
| 2008/0269714 A1 | 10/2008 | Mastrototaro et al. |
| 2008/0306353 A1 | 12/2008 | Douglas et al. |
| 2008/0319384 A1 | 12/2008 | Yodfat et al. |
| 2009/0112154 A1 | 4/2009 | Montgomery et al. |
| 2009/0164251 A1 | 6/2009 | Hayter |
| 2009/0204341 A1 | 8/2009 | Brauker et al. |
| 2010/0017141 A1 | 1/2010 | Campbell et al. |
| 2010/0049022 A1 | 2/2010 | Parris et al. |
| 2010/0057042 A1 | 3/2010 | Hayter |
| 2010/0075353 A1 | 3/2010 | Heaton |
| 2010/0082167 A1 | 4/2010 | Haueter et al. |
| 2010/0121170 A1 | 5/2010 | Rule |
| 2010/0137788 A1 | 6/2010 | Braithwaite et al. |
| 2010/0138097 A1 | 6/2010 | Ku et al. |
| 2010/0145262 A1 | 6/2010 | Bengtsson et al. |
| 2010/0174266 A1 | 7/2010 | Estes |
| 2010/0249561 A1 | 9/2010 | Patek et al. |
| 2010/0256466 A1 | 10/2010 | Shekalim et al. |
| 2010/0262117 A1 | 10/2010 | Magni et al. |
| 2010/0292634 A1 | 11/2010 | Kircher et al. |
| 2010/0295686 A1 | 11/2010 | Sloan et al. |
| 2010/0298765 A1 | 11/2010 | Budiman et al. |
| 2010/0317952 A1 | 12/2010 | Budiman et al. |
| 2011/0009725 A1 | 1/2011 | Hill et al. |
| 2011/0009813 A1 | 1/2011 | Rankers |
| 2011/0021898 A1 | 1/2011 | Wei et al. |
| 2011/0029034 A1 | 2/2011 | Fischer et al. |
| 2011/0098548 A1 | 4/2011 | Budiman et al. |
| 2011/0098674 A1 | 4/2011 | Vicente et al. |
| 2011/0106011 A1 | 5/2011 | Cinar et al. |
| 2011/0106050 A1 | 5/2011 | Yodfat et al. |
| 2011/0118987 A1 | 5/2011 | Takeuchi et al. |
| 2011/0160555 A1 | 6/2011 | Reifman et al. |
| 2011/0208156 A1 | 8/2011 | Doyle et al. |
| 2011/0264071 A1 | 10/2011 | Braig et al. |
| 2011/0266999 A1 | 11/2011 | Yodfat et al. |
| 2012/0010592 A1 | 1/2012 | Brown |
| 2012/0059351 A1 | 3/2012 | Nordh |
| 2012/0136336 A1 | 5/2012 | Mastrototaro et al. |
| 2012/0165638 A1 | 6/2012 | Duke et al. |
| 2012/0232520 A1 | 9/2012 | Sloan et al. |
| 2012/0246106 A1 | 9/2012 | Atlas et al. |
| 2012/0277667 A1 | 11/2012 | Yodat |
| 2012/0283694 A1 | 11/2012 | Yodfat et al. |
| 2012/0330227 A1 | 12/2012 | Budiman et al. |
| 2013/0030358 A1 | 1/2013 | Yodfat et al. |
| 2013/0046281 A1 | 2/2013 | Javitt |
| 2013/0072872 A1 | 3/2013 | Yodfat et al. |
| 2013/0079613 A1 | 3/2013 | Kovatchev et al. |
| 2013/0245547 A1 | 9/2013 | El-Khatib et al. |
| 2014/0066887 A1 | 3/2014 | Mastrototaro et al. |
| 2014/0128705 A1 | 5/2014 | Mazlish |
| 2014/0309615 A1 | 10/2014 | Mazlish |
| 2014/0350369 A1 | 11/2014 | Budiman et al. |
| 2015/0165117 A1 | 6/2015 | Palerm et al. |
| 2015/0289823 A1 | 10/2015 | Rack-Gomer et al. |
| 2017/0182248 A1 | 6/2017 | Rosinko |

FOREIGN PATENT DOCUMENTS

| | | |
|---|---|---|
| WO | 2006/124716 A3 | 3/2007 |
| WO | 2008/057384 A3 | 9/2008 |
| WO | 2008/157780 A1 | 12/2008 |
| WO | 2013/096769 A1 | 6/2013 |
| WO | 2014/035570 A2 | 3/2014 |
| WO | 2017/027459 A1 | 2/2017 |

OTHER PUBLICATIONS

Pennant et al.; Insulin administration and rate of glucose appearance in people with type 1 diabetes; Diabetes Care; 31(11); pp. 2183-2187; Nov. 2008.

Mudaliar et al.; Insulin aspart (B28 Asp-insulin): A fast-acting analog of human insulin; Diabetes Care; 22(9); pp. 1501-1506; Sep. 1999.

Leon-Vargas, F. et al.; "Postprandial blood glucose control using a hybrid adaptive PD controller with insulin-on-board limitation"; Biomedical Signal Processing and Control 8 (2013) 724-732.

International Search Report and Written Opinion, as issued in connection with International Patent Application No. PCT/US2015/034705, dated Sep. 4, 2015, 10 pages.

Frirst Examination Report for Autralian Application No. 2015274894, dated Feb. 22, 2018, five pages.

Extended European Search Report for European Patent Application No. 1580700.3, dated Jan. 22, 2018, 15 pages.

European Examination Report for European Application No. 14726270.3 dated Mar. 23, 2018, six pages.

Canadian Office Action for Canadian Application No. 2,950,966 dated Oct. 17, 2017, 3 pages.

Mark E. Pennant Ph.D. et al., "Insulin Administration and Rate of Glucose Appearance in People with Type 1 Diabetes"; Diabetes Care, Nov. 2008, vol. 31, No. 11, pp. 2183-2187.

Karena L. Swan M.D., et al., "Effect of Age of Infusion Site and Type of Rapid-Acting Analog on Pharmacodynamic Parameters of Insulin Boluses in Youth with Type 1 Diabetes Receiving Insulin Pump Therapy"; Diabetes Care, Feb. 2009, vol. 32 No. 2, pp. 240-244.

Cameron, Fraser, et al. "Statistical hypoglycemia prediction", Journal of diabetes science and technology;2.4 (2008):612-621. (Year: 2008).

European Communication pursuant to Article 94(3) EPC for European Application No. 15807000.3, dated Jan. 20, 2020, 13 pages.

Mazlish; U.S. Pat. App. entitled "Insulin delivery systems and methods," filed Jun. 8, 2015, U.S. Appl. No. 14/733,567.

Hovorka, Roman, et al. "Nonlinear model predictive control of glucose concentration in subjects with type 1 diabetes." Physiological measurement 25.4 (2004): 905. (Year: 2004).

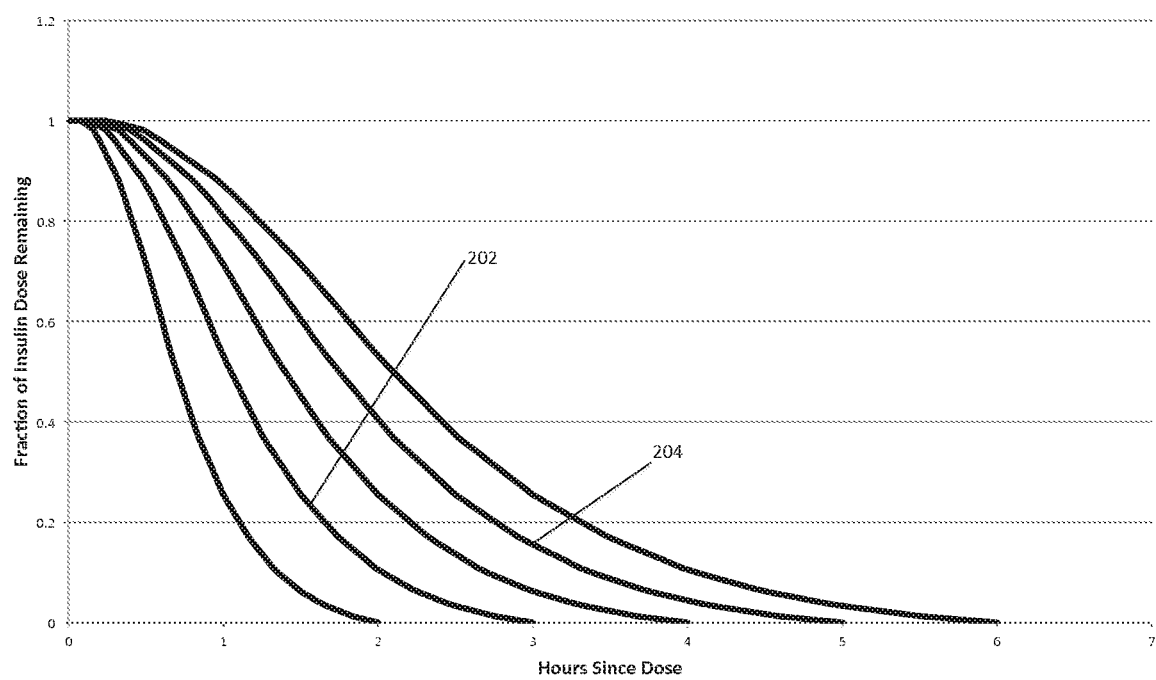

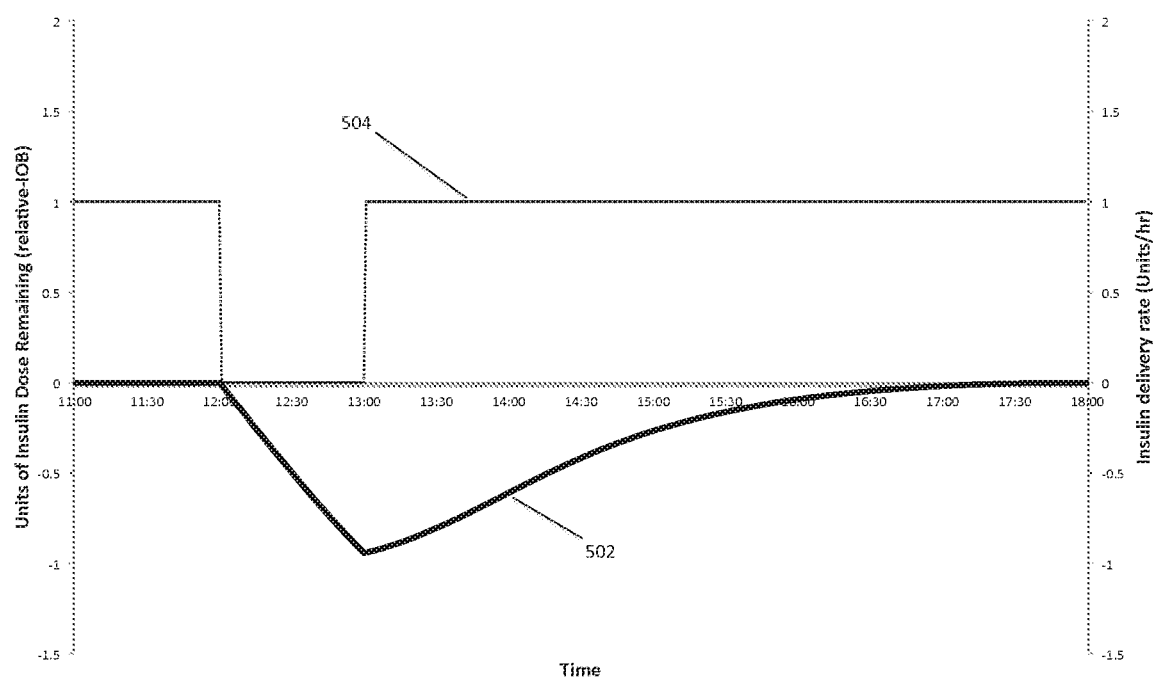

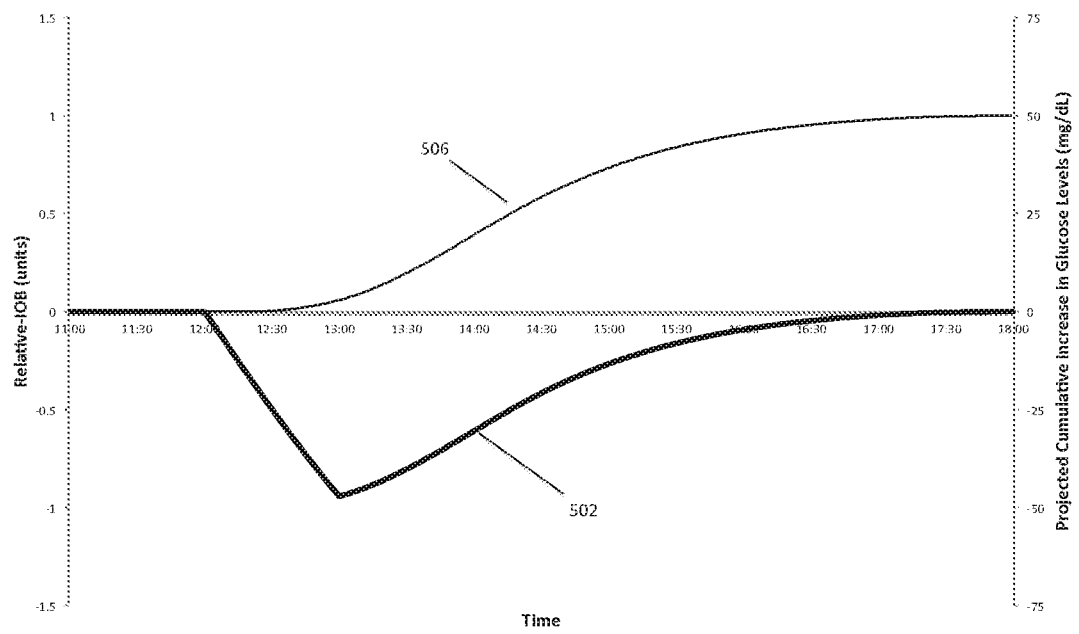

SYSTEMS FOR DETERMINING INSULIN ON BOARD AND RECOMMENDING INSULIN THERAPY AND RELATED METHODS

CROSS-REFERENCE TO RELATED APPLICATIONS

This application is a continuation of U.S. patent application Ser. No. 14/733,567, filed Jun. 8, 2015, which will issue as U.S. Pat. No. 10,188,793 on Jan. 29, 2019, entitled "INSULIN DELIVERY SYSTEMS AND METHODS," which claims the benefit of U.S. Provisional Application No. 62/010,385 filed Jun. 10, 2014 and entitled "INSULIN DELIVERY SYSTEMS AND METHODS," the entire contents and disclosure of which are hereby incorporated by this reference.

INCORPORATION BY REFERENCE

This application is related to U.S. patent application Ser. No. 14/254,684 filed Apr. 16, 2014 and entitled "Discretionary Insulin Delivery Systems and Methods", and U.S. patent application Ser. No. 13/738,466 filed Jan. 10, 2013, now U.S. Pat. No. 9,833,191, issued Dec. 5, 2017, and entitled "Computer-Based Diabetes Management". All publications and patent applications mentioned in this specification are herein incorporated by reference to the same extent as if each individual publication or patent application was specifically and individually indicated to be incorporated by reference.

TECHNICAL FIELD

This disclosure relates to the delivery of insulin to a user (e.g., a person with diabetes) and, more particularly, this disclosure relates to systems and methods for determining dosages of insulin to be delivered to a user.

BACKGROUND

Diabetes mellitus is a chronic metabolic disorder caused by an inability of a person's pancreas to produce sufficient amounts of insulin, such that the person's metabolism is unable to provide for the proper absorption of sugar and starch. This failure leads to hyperglycemia, i.e., the presence of an excessive amount of analyte within the blood plasma. Persistent hyperglycemia has been associated with a variety of serious symptoms and life threatening long term complications such as dehydration, ketoacidosis, diabetic coma, cardiovascular diseases, chronic renal failure, retinal damage and nerve damages with the risk of amputation of extremities. Because healing is not yet possible, a permanent therapy is necessary which provides constant glycemic control in order to constantly maintain the level of blood analyte within normal limits. Such glycemic control is achieved by regularly supplying external drugs to the body of the patient to thereby reduce the elevated levels of blood analyte.

An external biologically effective drug (e.g., insulin or its analog) was commonly administered by means of multiple, daily injections of a mixture of rapid and intermediate acting drug via a hypodermic syringe. While this treatment does not require the frequent estimation of blood analyte, it has been found that the degree of glycemic control achievable in this way is suboptimal because the delivery is unlike physiological drug production, according to which drug(s) enters the bloodstream at a lower rate and over a more extended period of time.

Improved glycemic control may be achieved by the so-called intensive drug therapy which is based on multiple daily injections, including one or two injections per day of a long acting drug for providing basal drug and additional injections of a rapidly acting drug before each meal in an amount proportional to the size of the meal. Although traditional syringes have at least partly been replaced by drug pens, the frequent injections are nevertheless very inconvenient for the patient, particularly those who are incapable of reliably self-administering injections.

Substantial improvements in diabetes therapy have been achieved by the development of other drug delivery devices, such as insulin pumps, relieving the patient of the need for syringes or drug pens and the administration of multiple, daily injections. Insulin pumps allow for the delivery of insulin in a manner that bears greater similarity to the naturally occurring physiological processes and can be controlled to follow standard or individually modified protocols to give the patient better glycemic control.

In addition, delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. External drug delivery devices are mounted on clothing, hidden beneath or inside clothing, or mounted on the body and are generally controlled via a user interface built-in to the device or on a separate remote device.

Drug delivery devices have been utilized to assist in the management of diabetes by infusing drug or a suitable biologically effective material into the diabetic patient at a basal rate with additional drug or "bolus" to account for meals or high analyte values, levels or concentrations. The drug delivery device typically is connected to an infuser, better known as an infusion set by a flexible hose. The infuser typically has a subcutaneous cannula, and an adhesive backed mount on which the cannula is attached. The cannula may include a quick disconnect to allow the cannula and mount to remain in place on the skin surface of the user while the flexible tubing is disconnected from the infuser. Regardless of the type of drug delivery device, blood analyte monitoring is typically required to achieve acceptable glycemic control. For example, delivery of suitable amounts of drug by the drug delivery device requires that the patient frequently determine his or her blood analyte level and manually input this value into a user interface for the external drug delivery device, which then may calculate a suitable modification to the default or currently in-use drug delivery protocol, i.e. dosage and timing, and subsequently communicates with the drug delivery device to adjust its operation accordingly. The determination of blood analyte concentration is typically performed by means of an episodic measuring device such as a hand-held electronic meter which receives blood samples via enzyme-based test strips and calculates the blood analyte value based on the enzymatic reaction. In recent years, continuous analyte monitoring has also been utilized with drug delivery devices to allow for greater control of the drug(s) being infused into the diabetic patients.

In 1993, the landmark Diabetes Complications and Control Trial (DCCT) showed that intensive control of blood glucose not only reduces but also can prevent complications from Type 1 Diabetes. Post-DCCT health care professionals began prescribing a basal and bolus regimen of intensive insulin therapy to patients to help them maintain better glycemic control.

Basal insulin is a constant or near constant dosage of insulin to provide the body with insulin to allow for processing of glucose to maintain the background metabolic function of the body. Basal insulin can be infused via a daily or twice daily dose of long-acting insulin where the insulin's availability and action is formulated to last for an extended period of time. Alternatively, the basal requirements of an individual may be provided by a constant infusion of rapid acting insulin analog via an insulin delivery device. An insulin bolus is a burst of rapid acting insulin to offset either a prandial event or to bring a patient's blood glucose level from hyperglycemia to the desired, target range. Typically, the bolus of insulin may be delivered subcutaneously through an insulin syringe, an insulin pen or via another insulin delivery device such as an insulin pump.

A person in glucose stasis will tend to remain so in the absence of any meal disturbances and if the person's acting basal insulin schedule exactly offsets the person's background metabolic needs for insulin. When there is an excess of basal insulin at work, then the person's blood glucose level will tend to decrease. A deficiency of basal insulin relative to what the person's body requires will result in an increase in blood glucose level. Often, a person is first diagnosed with diabetes upon finding a higher than normal, fasting blood glucose level; this is a sign of insufficient endogenous insulin production.

In the years since the DCCT, patients with type 1 diabetes have often struggled with managing the challenges of intensive insulin therapy. There are myriad variables that both affect a person's insulin requirements and how their dosing should change on a day to day basis and even within a day. In light of the many deficiencies and problems associated with current systems and methods for maintaining proper glycemic control, enormous resources have been put into finding better solutions. It has been contemplated for many years that it should be entirely feasible to couple a continuous glucose monitoring system with an insulin delivery device to provide some level of automation to the management of insulin delivery to people with diabetes. The effort in this domain has ranged from semi-automated systems to fully automated delivery systems; however, most systems have at least some level of user interaction. Further, in any of these systems, the user's role changes from direct actor to supervisor of the automated system. As such, the user requires new and different tools for overseeing such automation. The present disclosure includes novel systems and methods that assist the user in understanding and visualizing what actions automated insulin delivery systems are taking in an effort to maintain the patient's glycemic control.

BRIEF SUMMARY

According to some aspects of the disclosure, systems and methods are provided to assist a user of insulin therapy in using semi-automated and automated insulin delivery systems. The disclosure describes methods to quantify and visualize an arbitrary set of automated delivery actions as well as user programmed delivery actions.

In some embodiments, the methods compare the automated delivery actions to a reference insulin delivery schedule to calculate an estimated net amount of historical dosing action. This estimated amount may be used in the calculation of a bolus amount or may also be used to visualize the future effects of the automated dosing.

In some embodiments, a system is provided with an insulin delivery device and a computer-based control unit. The insulin delivery device is configured to deliver insulin to a user of the system. The computer-based control unit is associated with the insulin delivery device and includes a user interface and a computer-based processor. The computer-based processor is configured to calculate a relative insulin on board value for a specific time. It does this by calculating a first value that represents a reference insulin on board value at the specific time. It also calculates a second value that represents an automated insulin on board value at the specific time. The computer-based processor subtracts one of the first and second values from the other. The automated insulin on board value represents at least one insulin delivery automatically specified by the computer-based control unit.

In some of the above embodiments, the relative insulin on board calculation further includes adding a non-automated insulin on board value to the automated insulin on board value when calculating the second value. The non-automated insulin on board value represents at least one insulin delivery manually specified by the user or a caregiver. In some embodiments, the relative insulin on board calculation takes into account all insulin delivered to the user prior to the specific time that is believed to not have been completely absorbed by the user prior to the specific time, including any and all basal doses delivered to the user.

In some embodiments, a glucose monitor is configured to measure glucose values of the user. The glucose monitor is configured to automatically transfer the glucose values to the computer-based control unit. The computer-based control unit is configured with a mode to automatically control insulin delivery to the user through the insulin delivery device, thereby forming an automatic feedback control loop.

In some embodiments, the computer-based processor is configured to calculate the relative insulin on board value by subtracting the first value from the second value. The calculation of the first value may include all insulin delivered according to a reference insulin delivery schedule and the second value may include all insulin delivered according to an automated insulin delivery schedule. The reference insulin on board value may be greater than the automated insulin on board value. In some embodiments, the computer-based control unit is configured to display the relative insulin on board value on the user interface to the user or a caregiver. The computer-based control unit may be configured to display a function of the relative insulin on board value as it is calculated to vary over a time period. In some embodiments at least a portion of the time period is a future time. The computer-based control unit may also be configured to calculate and display a predicted change in glucose levels based on the function of the relative insulin on board value. In some embodiments, the computer-based control unit is configured to calculate a future insulin delivery schedule based in part on the relative insulin on board value calculated by the computer-based processor. The insulin delivery device may be configured to deliver insulin to the user of the system according to the calculated future insulin delivery schedule.

In some embodiments, a system is provided with an insulin delivery device and a computer-based control unit. The insulin delivery device is configured to deliver insulin to a user of the system. The computer-based control unit is associated with the insulin delivery device and includes a user interface and a computer-based processor. The computer-based processor is configured to calculate a relative insulin on board value over a period of time. This is accomplished by first calculating a difference-dosing-schedule. The difference-dosing-schedule is calculated by using a first schedule that represents a reference dosing and a second schedule that represents an automated dosing at each of a plurality of time points in the period of time. At each of the plurality of time points, one of the first and second schedule values at the time point is subtracted from the other. The relative insulin on board is then obtained by calculating an insulin on board value for the difference-dosing-schedule by summing an insulin on board for each of the plurality of time points. The automated dosing represents at least one insulin delivery automatically specified by the computer-based control unit.

In some of the above embodiments, the system further comprises a glucose monitor configured to measure glucose values of the user. The glucose monitor is configured to automatically transfer the glucose values to the computer-based control unit. The computer-based control unit is configured with a mode to automatically control insulin delivery to the user through the insulin delivery device, thereby forming an automatic feedback control loop.

In some embodiments, an insulin delivery device is provided with an insulin delivery mechanism and a computer-based control unit. The insulin delivery mechanism is configured to deliver insulin to a user of the device. The computer-based control unit is coupled to the insulin delivery mechanism to automatically deliver insulin to the user. The computer-based control unit has a user interface and a computer-based processor. The computer-based processor is configured to calculate a relative insulin on board value associated with a specific time period. This is accomplished by calculating a first value that represents a reference insulin on board value associated with the specific time period. A second value is calculated that represents an automated insulin on board value associated with the specific time period. One of the first and second values is subtracted from the other. The automated insulin on board value represents at least one insulin delivery automatically specified by the computer-based control unit. The reference insulin on board value may be greater than the automated insulin on board value. The computer-based control unit is configured to display the relative insulin on board value on the user interface to the user or a caregiver.

In some of the embodiments, the computer-based control unit further comprises a bolus calculator configured to assist the user or a caregiver with calculating a bolus dosage of insulin to be delivered to the user. The bolus calculator is configured to use the calculated relative insulin on board value in determining a proper bolus dosage.

In some embodiments, a method of delivering insulin to a user is provided. The method includes providing an insulin delivery device configured to deliver insulin to a user of the system. The method further includes providing a computer-based control unit associated with the insulin delivery device. The computer-based control unit has a user interface and a computer-based processor. The method further includes calculating a relative insulin on board value for a specific time. This is accomplished by calculating a first value that represents a reference insulin on board value at the specific time. A second value that represents an automated insulin on board value at the specific time is also calculated. One of the first and second values is subtracted from the other. The automated insulin on board value represents at least one insulin delivery automatically specified by the computer-based control unit. The method further includes calculating an insulin dosage schedule based in part on the calculated relative insulin on board value. The method also includes delivering insulin to the user according to the calculated insulin dosage schedule.

In some of the above embodiments, the method further includes displaying the calculated relative insulin on board value to the user or a caregiver on the user interface. The method may also include allowing the user or a caregiver to manually enter an insulin dosage into the computer-based control unit through the user interface to be subsequently delivered to the user after the calculated relative insulin on board value has been displayed on the user interface. In some embodiments, the reference insulin on board value may be greater than the automated insulin on board value.

BRIEF DESCRIPTION OF THE DRAWINGS

FIG. 2A is a plot showing one implementation of insulin absorption for multiple values of duration of insulin action.

FIG. 5A illustrates an exemplary calculation of insulin on board for the system in

FIG. 1.

FIG. 5B illustrates an exemplary visualization of future glucose changes for the system in FIG. 1.

DETAILED DESCRIPTION

Figure 1:
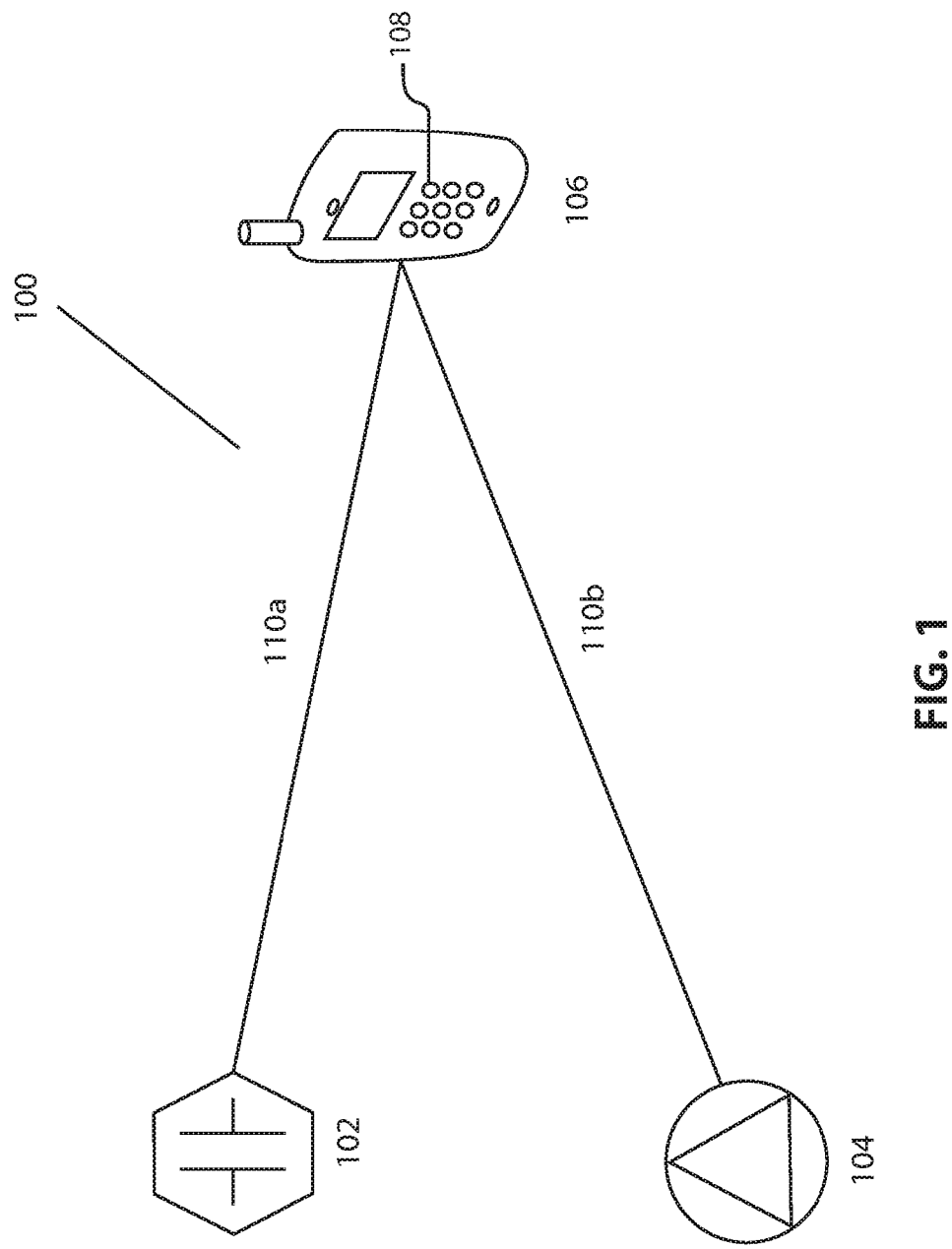
FIG. 1 is a schematic view of an exemplary system adapted to implement one or more of the techniques disclosed herein.

FIG. 1 is a schematic view of an exemplary system 100 adapted to implement one or more of the techniques disclosed herein.

The illustrated system 100 includes a glucose monitoring/measuring device 102, an insulin delivery device such as an insulin pump 104 and a controller 106. The controller 106 has a user interface 108, an internal computer-based processor and internal computer-based memory storage capacity.

In the illustrated implementation, the glucose monitoring/measuring device 102, the insulin pump 104 and the controller 106 are configured so that they can communicate with each other using wireless communication channels 110a, 110b (e.g., using wireless communication technologies). However, in other implementations, information may be transferred between the components illustrated in FIG. 1 using a wired connection or may, in some instances, be transferred by the user or caregiver him or herself. For example, if the glucose monitoring/measuring device 102 is a monitor that simply presents blood glucose reading on a visual display, for example, but is not able to transmit the reading directly to the controller 106, then the person using the system 100 may view the displayed blood glucose reading and enter that reading manually at the controller 106. In other implementations (not shown), any one of the glucose monitoring/measuring device 102, the insulin pump 104 and the controller 106 can be combined with another of the devices in a single integrated unit, or all three may be combined. For example, some implementations incorporate the controller 106 into the insulin delivery device 104. In combined devices, insulin delivery protocols may be provided by a dedicated computer-based processor, or a single processor may control the insulin delivery protocols, glucose monitoring, insulin delivery device functions and/or user interface functions.

In various implementations, the glucose monitoring/measuring device 102 can be a continuous glucose monitor, a blood glucose meter, an intravenous blood glucose measurement device, or other device adapted to provide an indication of blood glucose levels in the user. In some implementations, the level of glucose in the user's blood may never be directly measured. Rather, the glucose level in the user's interstitial fluid or other bodily fluid or tissue may be measured, and at some point may (or may not) be converted into an equivalent glucose level of whole blood, plasma or serum. It is to be understood that the use herein of the terminology "blood glucose" level may mean actual blood glucose level or a surrogate glucose level, depending on the context.

The insulin "pump" 104 can be any type of insulin delivery device. In general, the insulin pump is a medical device used for the administration of insulin, for example, in the treatment of diabetes. The pump can have a variety of possible configurations. In some implementations, for example, the insulin pump 104 includes a pump (with controls, processing module, batteries, etc.), a disposable reservoir for insulin (which may be inside the pump), and a disposable infusion set, including a cannula for subcutaneous insertion (under the skin) and a tubing system to interface the insulin reservoir to the cannula. In some implementations, however, the pump may not include one or more of these components. For example, in some implementations, the pump will not have tubing. Also, in some implementations, the pump will not include a disposable reservoir. In other configurations, the pump may be controlled by a handheld device or by an application loaded onto a mobile phone or other mobile computing device. It is to be understood that, depending on the context, the use herein of the terminology "pump" or "delivery device" may refer to conventional insulin pumps available on the market today, or may refer to other insulin delivery devices such as insulin pens, automated inhalers, variable rate insulin skin patches and other such delivery devices, whether or not they are commercially available today. It is envisioned that the devices, systems and methods disclosed herein may also be applied to other insulin delivery methods, such as intravenous insulin delivery in an intensive care unit, and may also find use in delivering other medicines or fluids to a user. In such other systems, analyte(s) other than glucose may be monitored in a user's body to aid in determining the desired amount of medicine or fluid to be delivered to the user.

The controller 106 can be any type of computer-based device configured to implement and/or facilitate the functionalities disclosed herein. In some implementations, the controller 106 is a smartphone executing the Android™ operating system. However, the controller 106 can be any type of smartphone (or other device) executing any type of operating system. In general, a smartphone is a mobile phone built on a mobile operating system, with more advanced computing capability connectivity than a feature phone. Many modern smartphones also include high-resolution touchscreens and web browsers that display web pages. High-speed data access can be provided by Wi-Fi and/or mobile broadband. In a typical implementation, the insulin delivery device 104 is adapted to deliver insulin to a user (e.g., a person with diabetes). Typically, the user has the ability to set a default basal insulin delivery schedule to provide a continuous, background dose of insulin to provide for the basic metabolic needs of the individual. The basal delivery, once set, will provide the pre-programmed dose of insulin unless directed otherwise by the user such as by suspending delivery or by instructing the insulin pump to deliver a temporary basal rate which differs from the pre-programmed rate for a period of time. A typical insulin pump implementation is also adapted to allow the user to program bolus doses of insulin, either to be delivered immediately or to be spread over a period of time, sometimes referred to as an extended bolus.

Semi-automated or automated systems may have a variety of modes in which they can operate. Typically, one of these modes is a default or zero-automation mode where the system provides no automation and the user is wholly responsible for their insulin dosing. In the default mode, an automated system provides a schedule of basal insulin delivery that we refer to as the default basal delivery program. The default mode may be triggered, for example, when the system does not have a continuous glucose sensor actively providing glucose information. Or it may be the result of some other condition that the system deems unsafe for automated delivery such as a degraded continuous glucose sensor signal.

The determination of what the default basal delivery program is may vary across implementations. In some implementations, the default basal delivery schedule can be a fixed schedule of insulin delivery that the user inputs. In other implementations, the system may vary the default basal delivery schedule over time to optimize the basal insulin that is delivered when the system operates in its default, zero-automation mode. In some implementations, the default basal program includes or consists of a vector of day-time pairs coupled with a rate of insulin delivery between that time period and the next time period.

As used herein, a "user" is typically a person who receives insulin from the inventive devices, systems and methods disclosed herein. In some implementations, actions may be performed by a "caregiver" who is a person or persons different from the "user". For example, the caregiver may be a parent, other family member, teacher, physician, clinician, advisor, or other person(s) assisting the user with management of his or her diabetes. In some implementations, actions ascribed to a caregiver must be performed by the caregiver(s) and may not be performed by the user. In other implementations, the user and the caregiver are one and the same person, and there is no other person directly involved in the delivery of insulin to the user.

In some implementations, the system 100 provides for automated delivery modes wherein the system is configured to automatically dose insulin. The automated or semi-automated algorithm that the system uses to determine the amount of insulin to deliver at any point in time may vary greatly across implementations. In a typical implementation, however, the user will find it valuable to gain some understanding of the nature of the automated insulin delivery; how much or how little insulin is being delivered and at what time it has been delivered. For example, a user may find this information valuable if the automation is only partial automation and the user is still required to make insulin dosing decisions concurrent with the automation. Another scenario where this information may be useful is when the system 100 finds it necessary to turn off the automation and switch to a default insulin delivery mode after which the user is solely responsible for managing the insulin delivery. In this situation, a user would find it helpful to understand what the automation has been doing up until the point of transition to manual-mode.

A key metric that patients using intensive insulin therapy rely upon to understand their insulin dosing is an estimate of how much insulin has been recently delivered to the user's body but has yet to act on the user's blood glucose level. This quantity is commonly referred to as insulin-on-board (IOB). The estimate of IOB is helpful to patients because it can take hours after insulin is delivered for the blood glucose lowering action of the insulin delivery to complete. During this time period, it may prove beneficial to a user to incorporate knowledge of this prior insulin delivery into the user's dosing decisions.

In a typical implementation, the system 100 can estimate IOB for the user based on information about recent actual insulin deliveries from the insulin delivery device 104 and insulin absorption information (e.g., the user's insulin absorption curve, and the user's duration of insulin action (DIA) which defines how long it takes for 100% absorption, etc.) that may be specific to the user.

Figure 2B:
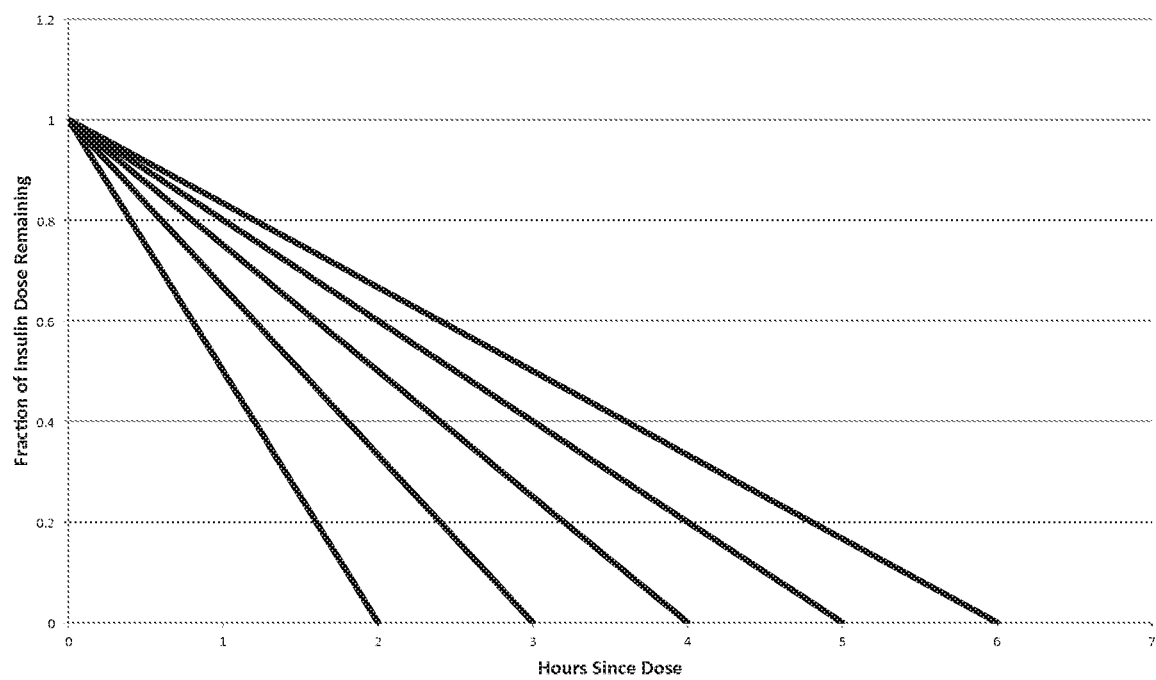
FIG. 2B is another plot showing linear implementation of insulin absorption for multiple values of duration of insulin action.

FIGS. 2A and 2B show illustrative examples of IOB absorption curves for various DIAs. The y-axes on the graphs show the fraction of insulin remaining on board from a dose of insulin and the x-axes show the hours elapsed since the delivery. Typically, the system 100 allows the user to configure the DIA to their specific insulin formulation and their personal response rate. For example, curve 202 shows an exemplary absorption profile for a DIA of 3 hours while curve 204 shows an absorption profile of 5 hours. The exemplary insulin action curves in FIG. 2A are adapted from Mudaliar, et al., "Insulin Aspart (B28 Asp-Insulin): A Fast-Acting Analog of Human Insulin," Diabetes Care 22:1501-1506, 1999. Other implementations may use other action curves such as a linear absorption profile as shown in FIG. 2B.

In traditional systems without any automation (i.e. systems that only provide a pre-programmed basal rate of insulin delivery and manually programmed bolus deliveries but no automated changes to the basal rate or automated bolus deliveries), insulin-on-board calculations typically do not include the basal rate insulin deliveries. Such basal deliveries typically are intended to maintain the current blood glucose level, not to raise or to lower it, and not to offset the effect of a meal, etc., as does a bolus delivery. As such, the basal rate of insulin can be considered an effective reference insulin delivery schedule that seeks to maintain static blood glucose levels. In implementations with automation, a reference schedule of insulin delivery is a useful tool to calculate the IOB of the automated deliveries.

A reference schedule of insulin delivery allows for incorporating both increases and reductions in insulin delivery into the IOB calculation. The methods described herein allow for a more complete understanding of automated or semi-automated insulin delivery by providing transparency into automated reductions in insulin delivery as well as increases in delivery. In some implementations, the default basal rate is used as a reference insulin delivery schedule, while other implementations may use a different insulin delivery schedule that may or may not be related to the default basal rate. Typically, the reference insulin delivery schedule is, to the best of the system's knowledge, the schedule of insulin delivery that will maintain a constant level of blood glucose in a steady state condition.

Typically, traditional IOB calculations do not include basal delivery because the basal delivery matches the reference insulin delivery schedule in these systems (to the best of the user's knowledge) and thus it should not have any effect (either to raise or to lower) on the user's blood glucose level regardless of how much basal insulin is "on-board." It follows that since the basal insulin deliveries are not expected to affect the user's blood glucose level, they aren't relevant to future dosing recommendations and should not be included in IOB calculations.

Considered another way, the reference insulin delivery schedule is the amount of insulin the system 100 would expect to exactly offset the user's metabolic needs to maintain blood glucose stasis absent any disturbances (such as meal, stress, etc.). Thus, although there may be basal insulin that has been dosed but has not yet been absorbed, a typical implementation would not anticipate the basal insulin dose to have any blood glucose lowering effect since it will be cancelled out by the metabolic needs of the person.

Typically, the calculation of insulin-on-board may include some or all of the following: meal related bolus insulin; correction related bolus insulin; extended bolus delivery; and, in some implementations, manually programmed temporary basal rates. A meal related bolus of insulin is a point dose of insulin taken primarily to offset the consumption of glucose increasing food such as carbohydrates. A correction related bolus delivery is a point in time dose of insulin that attempts to correct for a high blood glucose level back to the target range. An extended or square wave bolus is a bolus that is evenly dosed over a period of time, usually to offset a longer absorption meal. A temporary basal rate is a period of time when the user instructs the system 100 to deliver either more or less than the preset basal rate in the system.

Insulin on board for a point delivery of insulin (such as a bolus) may be determined by multiplying the amount of the insulin delivery by the fraction of absorption remaining as determined by the time since the delivery, the absorption curve and the DIA. A typical absorption curve will define a fraction of insulin remaining on the y-axis by the time since bolus on the x-axis as illustrated in FIGS. 2A and 2B.

Figure 3:
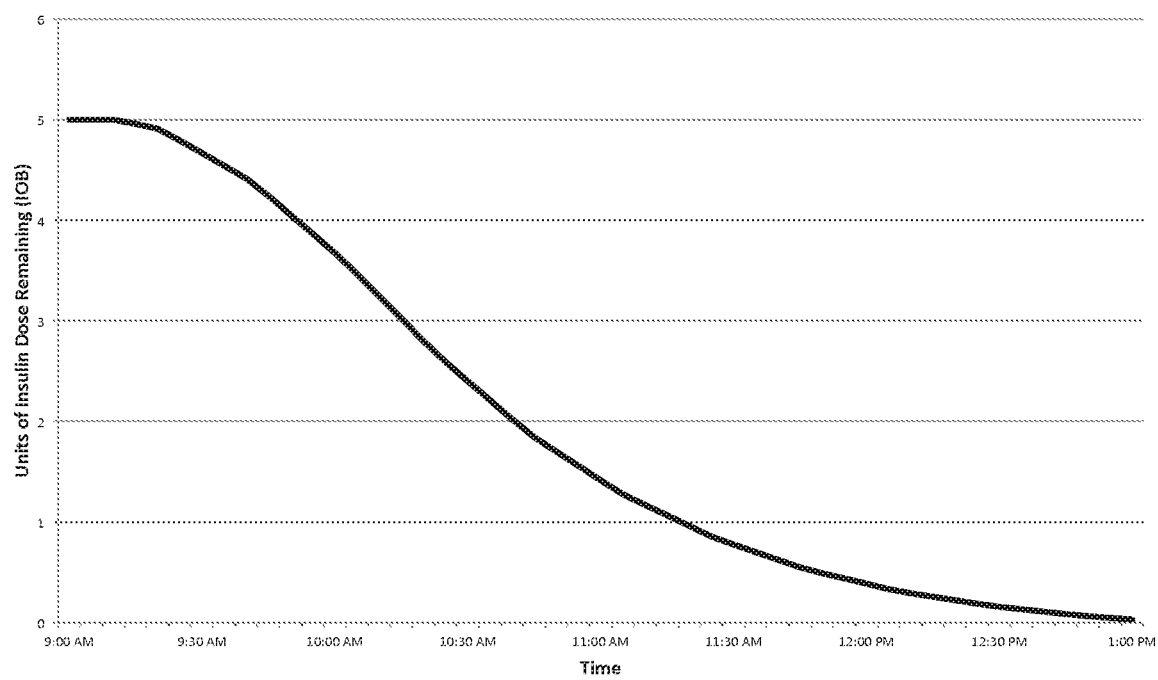
FIG. 3 is an exemplary representation of the behavior of the system in FIG. 1.

FIG. 3 shows an exemplary IOB calculation for a 5 unit bolus taken at 9:00 AM with the system configured to have a DIA of 4 hours. The y-axis is the insulin-on-board remaining from the bolus and the x-axis is the time. At 9:00 AM, the IOB equals the full 5 units of insulin since the dose was just given. By 10:30 AM, the IOB remaining is about 2.5 units. According to the illustrated example, the full insulin action of the bolus tails off around 1:00 PM or 4 hours after the bolus was initially given.

To calculate insulin on board for a continuous delivery of insulin such as a basal delivery or an extended bolus, the continuous delivery of insulin may be discretized into very small bolus deliveries of insulin. For example, if an extended bolus is given to dose 6 units of insulin over the next hour, the extended bolus delivery can be discretized into 60 boluses of 1/60th of the dose or 0.1 units each, delivered at minute 1, 2, 3, . . . , 60 of the hour. The exact interval of the discretization may vary across implementations and typically will work sufficiently well as long as the length of each sub-period is very small relative to the DIA. Once discretized, the IOB for each individual discretized bolus may be calculated as described above, and then summed together to compute the IOB for the entire continuous delivery. During the continuous delivery, only doses that have already occurred would be included in this calculation. Alternatively, if an implementation's insulin action curve may be represented by a mathematical function, it is possible to perform the above discrete integral by mathematically integrating the insulin action curve over the delivery period.

Figure 4:
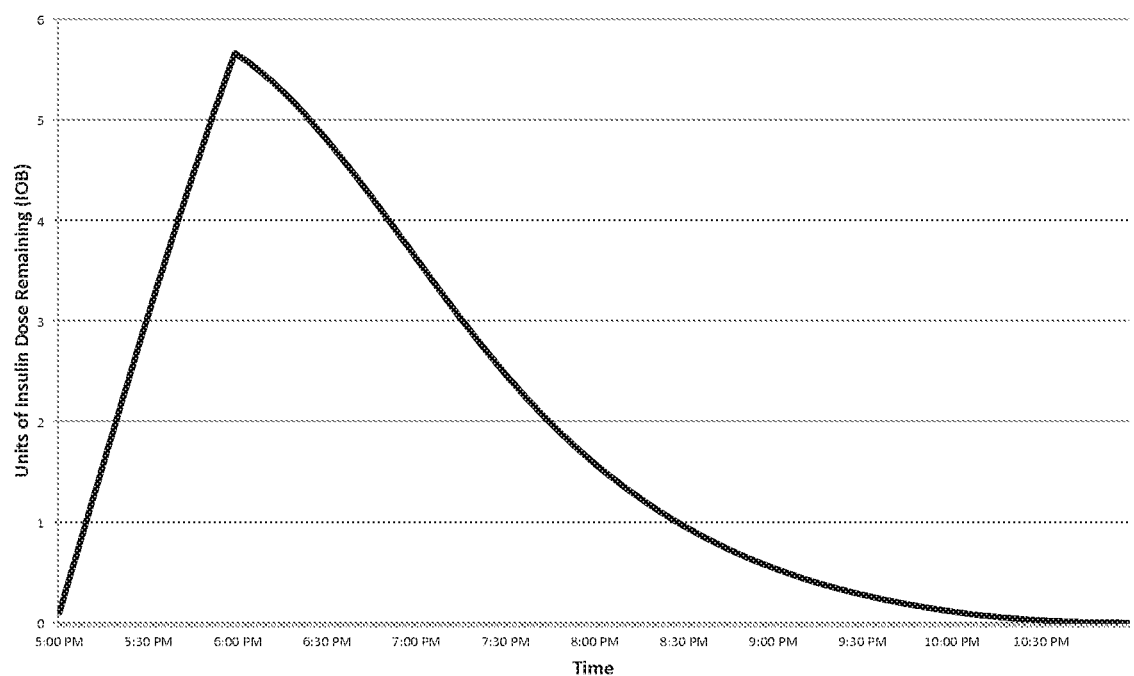
FIG. 4 is another exemplary representation of the behavior of the system in FIG. 1.

FIG. 4 illustrates the calculation of the IOB for the 6 unit extended bolus delivery discussed above. The 1 hour extended bolus is started at 5:00 PM with the DIA of the system 100 configured to be 5 hours. The IOB increases between 5:00 PM and 6:00 PM as the insulin is dosed. At 6:00 PM, the IOB is less than the full 6 units because some of the action of the insulin dosed between 5:00 PM and 6:00 PM has already completed. The IOB drops to about 3 units remaining at approximately 7:15 PM showing that about half of the absorption is complete at that time. The IOB does not return to 0 until around 11:00 PM when the 5 hour DIA for the final discretized boluses at 6 PM complete.

In some implementations, the system 100 allows for semi-automated or automated insulin dosing. As noted above, an implementation with automation may compute the IOB for the insulin delivered as part of the automated delivery. In some implementations, this IOB may be presented as an independent automated delivery IOB calculation while in other implementations, the automated delivery IOB is summed with the other, manual delivery IOB calculations to give a net total IOB calculation.

To calculate the IOB for semi-automated or automated dosing systems, some implementations will compare the actual automated insulin dosing history to the reference delivery schedule over the automated delivery time period to find the difference between the two. Typically, if the automated insulin delivery differs from the reference insulin delivery schedule, the system would expect there to be a residual blood glucose effect that should be reflected in an IOB calculation. This residual effect may be either positive or negative depending on how much and when the automated dosing occurred relative to the reference insulin delivery. Calculating the IOB in this manner will be referred to as a relative-IOB.

For example, take an automated delivery that allows the basal rate to vary between x and y units per hour where the reference delivery schedule would call for z units of basal delivery per hour. Some implementations calculate a relative-IOB for this type of automated delivery by computing the IOB for both the automated delivery IOB_automated) and for the reference delivery over the same time period (JOB reference) and then taking the difference, IOB_automated-IOB_reference to find the relative-IOB to assign to the period of the automated delivery. Typically, the IOB_automated and IOB_reference calculations will include all insulin dosing including basal insulin doses during the time period under consideration. The same calculation may be performed by first taking the difference between the automated delivery and the reference delivery schedules to create a difference-in-delivery schedule. The IOB may be calculated on the difference-in-delivery schedule to compute the relative-IOB for the automated delivery. That is, the relative-IOB calculation holds under the distributive property of mathematics. It will be apparent to those of ordinary skill in this art that other variations to these calculations may be made without departing from the scope and spirit of the appended claims. Note that in cases where the IOB_automated is less than the IOB_reference, the relative-IOB calculated for such automated delivery period is negative. A negative relative-IOB may be added to any other IOB from other deliveries (positive or negative) in a simple additive manner to calculate the total IOB for the user.

A negative relative-IOB reflects that the user has received less insulin than the reference delivery would have delivered. Since standard insulin therapy provides for the reference basal delivery to keep glucose values at static levels, the delivery of less than the reference basal delivery results in a deficit of insulin relative to what the user would need to keep glucose levels static. This deficit results in an expected subsequent rise in glucose values. The magnitude of this expected rise equals the absolute value of the insulin deficit amount, or relative-IOB, multiplied by the user's insulin sensitivity factor (ISF), where the ISF is the amount that a user's blood glucose level will decrease when dosed with 1 unit of insulin.

In some implementations, the benefit of computing the relative-IOB of an automated delivery is that it allows the user or caregiver to more easily understand and quantify what the net effect is of the therapy changes caused by a particular automated delivery. Depending on the implementation and the scenario, the particular automated delivery may deliver more or less than the reference delivery schedule. The relative-IOB calculation allows the user to see if the net effect of the automated delivery is an increase (positive JOB) or decrease (negative JOB) to the reference insulin delivery schedule and what the magnitude of such change is.

FIGS. 5A and 5B show an example relative-IOB calculation for a temporary attenuation of insulin delivery. This scenario could occur for example during an automated attenuation of insulin delivery or a manual temporary basal rate set by the user. In the illustrated example, the basal insulin delivery is attenuated by the automated system due to a decline in glucose levels. The DIA is configured to be 5 hours in the illustrated system.

Referring to FIGS. 5A and 5B the left y-axes show the calculated relative-IOB for the automated attenuation of delivery as illustrated by line 502. The x-axes show the time of day. The right y-axis in FIG. 5A shows the rate of insulin delivery in units per hour. In this illustrated example, the reference delivery rate is 1 unit per hour and the automated delivery schedule is shown by dashed line of 504. The right y-axis in FIG. 5B illustrates the cumulative expected change in blood glucose level for a user with an ISF of 50 mg/dL/unit, as illustrated by curve 506.

In the illustrated example, FIG. 5A shows the attenuation of insulin commences at 12:00 when the insulin delivery rate drops from 1 unit per hour to 0 units per hour. Line 502 shows that the absolute magnitude of the relative-IOB increases as the time period continues until 13:00 where the attenuation ceases and the delivery rate once again matches the reference basal delivery rate of 1 unit per hour. In this illustrated example, because the automated delivery is less than the reference delivery of 1 unit per hour, the calculated IOB for the automated delivery is less than the calculated IOB for the reference delivery. This results in a negative relative-IOB, implying that the blood glucose level is expected to rise as a result of the attenuation of insulin delivery.

FIG. 5B shows, in curve 506, the cumulative expected rise in blood glucose level that is implied by the negative relative-IOB illustrated by line 502. The effects of the attenuation begin to appear at approximately 12:40 when the effects of the first missing doses of insulin would have begun to act. The effect of the insulin attenuation increases substantially between 13:00 and 15:00 and continues to show small effects until the DIA of the last missing dose is reached at about 18:00.

The illustrated example shows how this relative information may be useful to a user. In the case of an automated insulin delivery attenuation, the missing insulin, relative to the reference delivery, will continue to have an effect for hours to come. If, for example, the automated attenuation was a result of a user's blood glucose level being near hypoglycemic levels, the negative relative-IOB could give the user information that may be helpful in reducing or even to dispensing with a carbohydrate ingestion intervention to raise blood glucose levels since the relative-IOB already implies a future rise in blood glucose levels. In another scenario where the user plans to eat a meal, knowledge that an insulin delivery attenuation may have already offset a low blood glucose level may be helpful to a bolus calculator which would otherwise reduce the prandial insulin bolus to account for the low blood glucose level.

The incorporation of the future effects of an attenuation of insulin such as illustrated in FIGS. 5A and 5B are not possible with the standard calculation of IOB that one will find discussed in prior art. The novel inclusion of both a reference insulin delivery schedule and the actual insulin delivery in the calculation of the IOB allows for automated attenuations of insulin to be seamlessly integrated into a user's bolus calculations and insulin therapy decisions. More accurate estimates of IOB will result in superior outcomes than in systems where such reductions in insulin delivery are excluded from the IOB calculation.

Figure 6A:
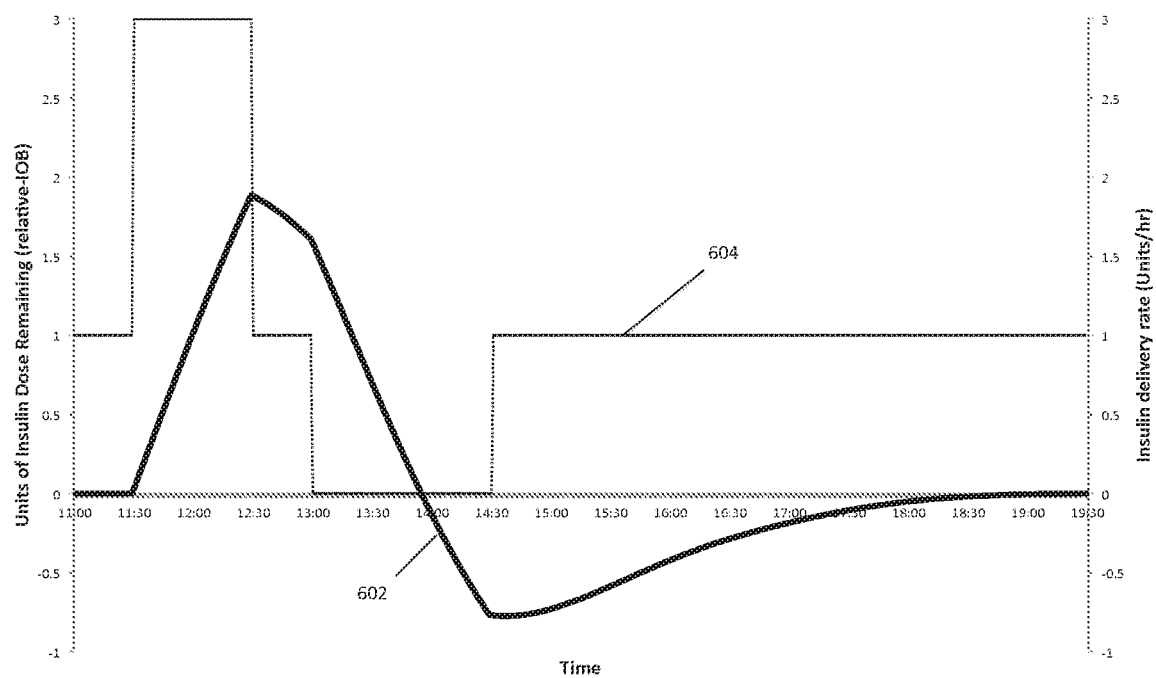
FIG. 6A illustrates another exemplary calculation of insulin on board for the system in FIG. 1.
Figure 6B:
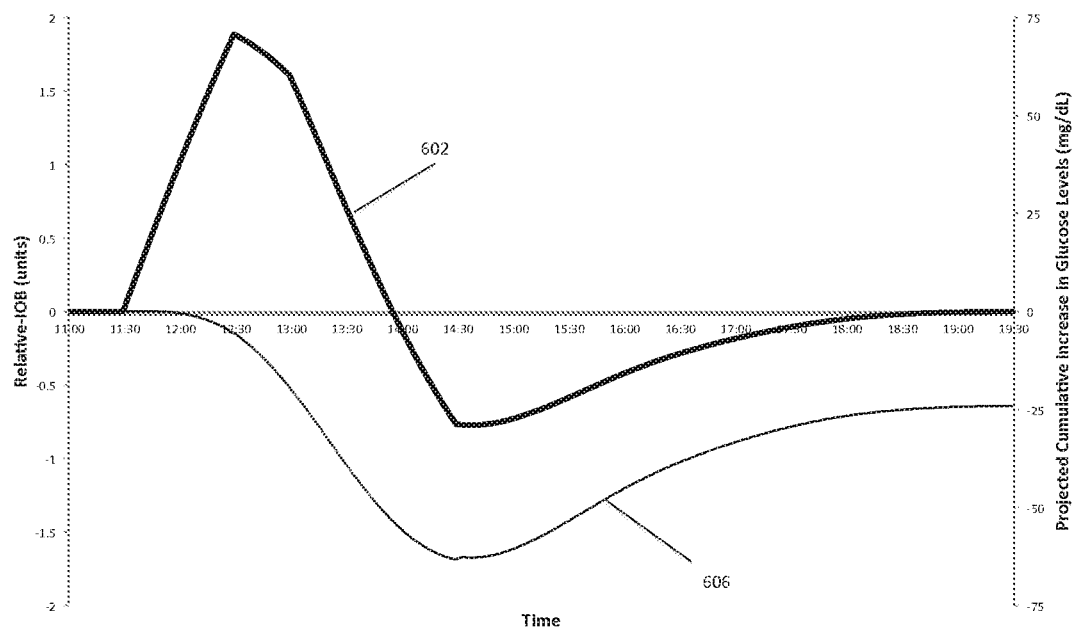
FIG. 6B illustrates another exemplary visualization of future glucose changes for the system in FIG. 1.

FIGS. 6A and 6B illustrate yet another example of the calculation of relative-IOB for automated insulin delivery. In the exemplary system, the system 100 is configured to have a DIA of 5 hours and a reference basal delivery of 1 unit per hour. The x-axes show the time of day. The left y-axes show the calculated relative-IOB for the automated delivery at each point in time, as illustrated by curve 602. The right y-axis in FIG. 6A shows the rate of automated insulin delivery as illustrated by dashed line 604, and the right y-axis in FIG. 6B shows the projected cumulative change in glucose levels from the start of the example at 11:00, as illustrated by curve 606.

Referring to FIG. 6A, we see that the automated system increases the insulin delivery rate from the reference level of 1 unit per hour to 3 units per hour at 11:30. This rate is held for 1 hour until 12:30. As shown by curve 602, the relative-IOB at 12:30 has risen from 0 to almost 2 units. The 2 units of IOB reflects the additional 2 units per hour that the automated delivery has provided between 11:30 and 12:30 that is over and above the reference delivery rate. The relative-IOB is less than 2 units at 12:30 because some of the addition insulin delivered has already acted.

Between 12:30 and 13:00 the relative-IOB (see curve 602) decreases as the insulin works to lower the blood glucose level as illustrated by curve 606 in FIG. 6B. At 13:00, the system attenuates insulin delivery to 0 units per hour. This immediately begins to decrease the relative-IOB for the user as can be seen by the sharp change in the rate of decline of curve 602 at 13:00. Between 13:00 and 14:30 the automated delivery rate is 0. During this time period, the calculated relative-IOB (see curve 602) is decreasing rapidly as the initial augmented dosing acts on the glucose levels and the negative relative-IOB from the attenuation is added to the IOB calculation, both causing a decrease in the net relative-IOB (see curve 602).

The change in glucose levels, as illustrated by curve 606 in FIG. 6B, continues to decrease even after the relative-IOB becomes negative just before 14:00. At this point, the glucose levels have been lowered by about 56 mg/dL due to the initial increase in insulin dosing. As the negative, relative-IOB (see curve 602) increases in magnitude, the effects of the insulin attenuation turn the blood glucose level plot (see curve 606) to a positive slope. The projected change in glucose level (curve 606) reaches a nadir at approximately 14:30, after which the glucose levels shown by curve 606 increase in line with the remaining negative, relative-IOB (see curve 602) from the insulin attenuation.

The illustrated example provides a simple window into the power of how the methods described herein can help to distill the salient effects of a complex set of automated dosing history that a typical automated or semi-automated implementation of the system 100 may engage in. Additionally, the methods may be used to combine both automated and manual insulin dosing histories seamlessly. The methods are agnostic as to the agent, human or machine, that takes the dosing or attenuation action. The methods described herein may be used to sum virtually any combination of automated insulin dosing including, but not limited to: meal boluses; correction boluses; an increase or decrease in basal rate (either automated or manual); and extended boluses. The methods may effectively incorporate basal rate differences of any magnitude and the changes in the exemplary systems in FIGS. 5A, 5B, 6A and 6B are for illustrative purposes only.

FIGS. 6A and 6B again show the limitations of prior art of IOB calculation. A standard calculation of IOB only incorporates insulin dosing greater than the pre-programmed basal rate (e.g., boluses) and does not take into account basal rate changes. As illustrated in FIGS. 6A and 6B, an automated or semi-automated system may have a complex set of automated actions that includes both increases and decreases of insulin delivery relative to a reference insulin delivery schedule. A system without the ability to integrate both increases and attenuations of insulin into the IOB calculation will not be able to accurately report the true IOB in an individual. The methods described herein can incorporate virtually any combination of increased, decreased, automated or manual dosing changes into the calculation of IOB and thus will be a valuable addition to the art and to future semi-automated and automated systems.

The methods may be further used to visualize the projected future action of the prior dosing (automated, manual or a combination of the two) as shown by curves 506 and 606 in FIGS. 5B and 6B, respectively. The future glucose level projections may be created by calculating the projected change in IOB at each future time period and then by multiplying the change by the user's ISF. This multiplication will give a projected change in blood glucose level vector for each future period of time. In these implementations, the projected change in IOB for a time period is the increase or decrease in IOB for all dosing adjustments administered prior to the time period. The IOB for a future time may be calculated using the standard IOB calculation but using a future time in lieu of the present time for the insulin absorption lookup on the insulin absorption curve. A cumulative projected glucose change curve such as curves 506 and 606 in FIGS. 5B and 6B, respectively, may be calculated by summing the set of future periods of interest.

In some implementations, the relative-IOB for automated dosing may be provided to a user separate and apart from the IOB from the manually programmed user doses. In other implementations, all of the IOB's for the system are combined together to provide a net IOB for the user. These values may be particularly useful if integrated into a bolus wizard or calculator.

A bolus calculator is a tool found in a typical insulin delivery device that helps a user to determine a correct insulin dose at a particular point in time based on a number of variables. The calculator may be used to determine if a correction dose is required and/or how many units of insulin should be taken for a certain amount of carbohydrates to be ingested. In a typical implementation, the bolus calculator uses a user's current blood glucose level, target glucose level, anticipated carbohydrates to be ingested and the current insulin on board for the user. How these variables are used in the calculation of the suggested bolus varies from implementation to implementation.

The use of the relative-IOB of automated dosing may be beneficial in many cases for users of insulin bolus calculators. As described herein, the relative-IOB resulting from automated deliveries may have a material effect on a user's future blood glucose level and thus including it in the bolus calculator may prove beneficial to the user. How the relative-IOB is used may vary among implementations: an implementation may choose to combine all IOB or it may consider the human dosed IOB differently from the automated, relative-IOB. The introduction of negative IOB's may further differentiate how different implementations choose to implement the information into their bolus recommendations. Some implementations may consider the negative relative-IOB contributions differently from the positive relative-IOB contributions.

In other implementations, the previously described automated delivery and associated automated IOB may be replaced with an "overall" delivery and associated overall JOB. In some embodiments, this overall delivery includes both the automated delivery and the manual delivery of insulin scheduled by the user or caregiver. For example, an overall delivery could include a temporary basal rate of x units of insulin per hour that is manually specified to be different from a reference delivery schedule of z units of basal delivery per hour. In these implementations, a relative-IOB for this type of overall delivery is calculated by computing the IOB for both the overall delivery IOB_overall) and for the reference delivery over the same time period GOB reference) and then taking the difference, IOB_overall-IOB_reference to find the relative-IOB to assign to the period of the overall delivery. Typically, the IOB_overall and IOB_reference calculations will include all insulin dosing including basal insulin doses during the time period under consideration. The same calculation may be performed by first taking the difference between the overall delivery and the reference delivery schedules to create a difference-in-delivery schedule. The IOB may be calculated on the difference-in-delivery schedule to compute the relative-IOB for the overall delivery. That is, the relative-IOB calculation holds under the distributive property of mathematics. It will be apparent to those of ordinary skill in this art that other variations to these calculations may be made without departing from the scope and spirit of the appended claims. In some of these implementations, the overall insulin on board value takes into account all insulin delivered to the user prior to a specific time that is believed to not have been completely absorbed by the user prior to that specific time, including any and all basal doses delivered to the user.

A number of embodiments of the present disclosure have been described. Nevertheless, it will be understood that various modifications may be made without departing from the spirit and scope of the disclosure.

For example, this specification contains many specific implementation details. However, these should not be construed as limitations on the scope of any inventions or of what may be claimed, but rather as descriptions of features specific to particular embodiments of the present disclosure. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings and descriptions in a particular order, this should not be understood as requiring that such operations be performed in the particular order shown or described, or in sequential order, or that all illustrated or described operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Processors suitable for the execution of a computer program include, by way of example, both general and special purpose microprocessor structures, and any one or more processors of any kind of digital computer. Generally, a processor will receive instructions and data from a read only memory or a random access memory or both. The elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical discs, or optical discs. However, a computer need not have such devices. Moreover, a computer can be embedded in another device, e.g., an insulin pump, an electronic pump controller, a continuous glucose monitor, a mobile telephone or a personal digital assistant (PDA), to name just a few.

Devices suitable for storing computer program instructions and data include all forms of non volatile memory, media and memory devices, including, by way of example, semiconductor memory devices, e.g., EPROM, EEPROM, and flash memory devices; magnetic discs, e.g., internal hard disks or removable disks; magneto optical discs; and CD ROM and DVD-ROM discs. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser. Thus, a user interface of the inventive systems and methods described herein may be remote from a computer-based processor of the system, and may be operated by a user and/or a caregiver.

Aspects of the disclosure can take the form of an entirely hardware embodiment, an entirely software embodiment or an embodiment containing both hardware and software elements. In some embodiments, aspects of the disclosure are implemented in software, which includes, but is not limited to, firmware, resident software, microcode, etc. Furthermore, the aspects of the disclosure can take the form of a computer program product accessible from a computer-usable or computer-readable medium providing program code for use by or in connection with a computer or any instruction execution system. For the purposes of this description, a computer-usable or computer-readable medium can be any tangible apparatus that can contain, store, communicate, propagate, or transport the program for use by or in connection with the instruction execution system, apparatus, or device.

As used herein, a computer-readable medium or computer-readable storage medium, or the like, is intended to include hardware (e.g., registers, random access memory (RAM), non-volatile (NV) storage, to name a few), but may or may not be limited to hardware. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disc. Current examples of optical discs include compact disc-read-only memory (CD-ROM), compact disc-read/write (CD-R/W). Some portions of the detailed description may be presented in terms of algorithms and symbolic representations of operations on data or data bits that may be, for example, within a computer memory. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that these and similar terms are to be associated with the appropriate physical quantities and are merely convenient labels applied to these quantities. Unless specifically stated otherwise or as apparent from context, it is appreciated that throughout the description, discussions utilizing terms such as "processing" or "computing" or "calculating" or "determining" or "displaying" or the like, refer to the action and processes of a computer system, or similar electronic computing device, computer-based processor, etc., which manipulates and transforms data represented as physical (electronic) quantities within the computer system's registers and memories into other data similarly represented as physical quantities within the computer system's memories or registers or other such information storage, transmission or display devices.

Other embodiments are within the scope of the appended claims.

What is claimed is:

1. A computer-implemented insulin delivery assistance system, comprising:
    a control unit:
    a non-transitory computer-readable storage medium storing instructions thereon that, when executed by the control unit, cause the computer-implemented insulin delivery assistance system to:
        receive blood glucose levels of a patient and insulin delivery information, wherein the insulin delivery information comprises information about automated or semi-automated insulin delivery to the patient over time;
        determine an estimated insulin-on-board (JOB) responsive to the insulin delivery information; and
        obtain a relative IOB that represents a difference between a reference IOB and the estimated JOB, the reference IOB representing an amount of insulin required to maintain blood glucose stasis of the patient; and
    a bolus calculator configured to determine a suggested bolus dose of insulin for a correction bolus or for a meal bolus, wherein the bolus calculator is configured to determine the suggested bolus dose of insulin by performing operations comprising:
        determining that a change to basal insulin delivery to the patient might affect future blood glucose levels based, at least in part, on the relative JOB; and
        determining if the suggested bolus dose of insulin is necessary based on modeling data.

2. The system of claim 1, wherein the bolus calculator is configured to provide the suggested bolus dose of insulin to the patient responsive to determining that the suggested bolus dose of insulin is necessary.

3. The system of claim 1, wherein the bolus calculator is configured to discard the suggested bolus dose of insulin responsive to determining that the suggested bolus dose of insulin is not necessary.

4. The system of claim 1, wherein the bolus calculator is configured to:
    obtain a first set of projected blood glucose levels based, at least in part, on an anticipated meal intake; and
    obtain a second set of projected blood glucose levels responsive to the determining that the change to basal insulin delivery might affect future blood glucose levels.

5. The system of claim 4, wherein the bolus calculator is configured to determine a meal bolus dose based, at least in part, on a difference between the second set of projected blood glucose levels and a target blood glucose level.

6. The system of claim 1, wherein the bolus calculator is configured to determine a correction dose of insulin responsive to determining that a received blood glucose level is outside a target range for blood glucose levels.

7. The system of claim 1, wherein the change to basal insulin delivery is an increase to basal insulin delivery or a decrease to basal insulin delivery.

8. The system of claim 1, wherein the bolus calculator is configured to determine that the suggested bolus dose of insulin is necessary to keep blood glucose levels of a patient within a target range for blood glucose levels responsive to determining that delivery of the suggested bolus dose of insulin will compensate for received blood glucose levels outside the target range for blood glucose levels to be within the target range for blood glucose levels.

9. The system of claim 1, wherein the bolus calculator is configured to determine that the suggested bolus dose of insulin is necessary to keep blood glucose levels of a patient within a target range for blood glucose levels responsive to determining that delivery of the suggested bolus dose of insulin will compensate for projected increased blood glucose levels due to anticipated meal intake to be within the target range for blood glucose levels.

10. A computer-implemented method for assisting with insulin delivery, comprising:
- receiving sensor blood glucose data of a patient and insulin delivery data, wherein the insulin delivery data comprises data corresponding to automated or semi-automated insulin delivery to the patient over time;
- determining an estimated insulin-on-board (JOB) responsive to the insulin delivery data and the sensor blood glucose data;
- obtaining a relative IOB responsive to a difference between a reference IOB and the estimated JOB, the reference IOB representing an amount of insulin required to maintain blood glucose stasis of the patient;
- determining a suggested bolus dose of insulin for a correction bolus or for a meal bolus;
- determining that a change to basal insulin delivery to the patient might affect future blood glucose levels based, at least in part, on the relative JOB; and
- determining if the bolus dose of insulin is necessary.

11. The method of claim 10, further comprising providing the suggested bolus dose of insulin to the patient responsive to determining that the suggested bolus dose of insulin is necessary.

12. The method of claim 10, further comprising discarding the suggested bolus dose of insulin responsive to determining that the suggested bolus dose of insulin is not necessary.

13. The method of claim 10, further comprising:
- obtaining a first projected blood glucose levels based, at least in part, on an anticipated meal intake; and
- obtaining a second projected blood glucose levels responsive to the determining that the change to basal insulin delivery might affect future blood glucose levels.

14. The method of claim 13, further comprising determining a meal bolus dose based, at least in part, on a difference between the second projected blood glucose level and a target blood glucose level.

15. The method of claim 10, further comprising determining a correction dose of insulin responsive to detecting that an estimated blood glucose level is outside a target range for blood glucose levels.

16. The method of claim 10, wherein the determining that a change to basal insulin delivery might affect future blood glucose levels comprises: detecting an increase to basal insulin delivery responsive to the relative JOB; or detecting a decrease to basal insulin delivery responsive to the relative JOB.

17. The method of claim 10, wherein the determining whether the suggested bolus dose of insulin is necessary comprises determining that the suggested bolus dose of insulin is necessary to keep blood glucose levels of a patient within a target range for blood glucose levels responsive to determining that delivery of the suggested bolus dose of insulin will compensate for received blood glucose levels outside the target range for blood glucose levels to be within the target range for blood glucose levels.

18. The method of claim 10, wherein the determining whether the suggested bolus dose of insulin is necessary comprises determining that the suggested bolus dose of insulin is necessary to keep blood glucose levels of a patient within a target range for blood glucose levels responsive to determining that delivery of the suggested bolus dose of insulin will compensate for projected increased blood glucose levels due to anticipated meal intake to be within the target range for blood glucose levels.

* * * * *

UNITED STATES PATENT AND TRADEMARK OFFICE
CERTIFICATE OF CORRECTION

PATENT NO. : 11,376,362 B2
APPLICATION NO. : 16/213799
DATED : July 5, 2022
INVENTOR(S) : Bryan Mazlish It is certified that error appears in the above-identified patent and that said Letters Patent is hereby corrected as shown below:

In the Specification

| | | |
|---|---|---|
| Column 6, | Line 47, | change "pump 104" to --pump (or insulin delivery device) 104-- |
| Column 9, | Line 11, | change "(JOB)" to --(IOB)-- |
| Column 12, | Line 21, | change "JOB) or decrease (negative JOB)" to --IOB) or decrease (negative IOB)-- |
| Column 11, | Line 43, | change "IOB_automated)" to --(IOB_automated)-- |
| Column 11, | Line 45, | change "(JOB reference)" to --(IOB_reference)-- |
| Column 15, | Line 25, | change "JOB" to --IOB-- |
| Column 15, | Lines 33-34, | change "IOB_overall)" to --(IOB_overall)-- |
| Column 15, | Line 35, | change "GOB reference)" to --(IOB_reference)-- |

In the Claims

| | | | |
|---|---|---|---|
| Claim 1, | Column 18, | Line 8, | change "(JOB)" to --(IOB)-- |
| Claim 1, | Column 18, | Line 11, | change "JOB" to --IOB-- |
| Claim 1, | Column 18, | Line 22, | change "JOB" to --IOB-- |
| Claim 10, | Column 19, | Line 7, | change "(JOB)" to --(IOB)-- |
| Claim 10, | Column 19, | Line 11, | change "JOB" to --IOB-- |
| Claim 10, | Column 19, | Line 18, | change "JOB" to --IOB-- |
| Claim 13, | Column 19, | Line 29, | change "levels" to --level-- |
| Claim 13, | Column 19, | Line 31, | change "levels" to --level-- |
| Claim 16, | Column 20, | Line 12, | change "JOB" to --IOB-- |
| Claim 16, | Column 20, | Line 14, | change "JOB" to --IOB-- |

Signed and Sealed this
Fourteenth Day of March, 2023

Katherine Kelly Vidal
*Director of the United States Patent and Trademark Office*